United States Patent [19]

Citrin et al.

[11] Patent Number: 4,589,870

[45] Date of Patent: May 20, 1986

[54] INCREMENTAL ACTUATOR FOR SYRINGE

[75] Inventors: Paul S. Citrin, Danbury; Nelson F. Murcko, Stratford, both of Conn.

[73] Assignee: Indicon, Inc., Brookfield, Conn.

[21] Appl. No.: 581,801

[22] Filed: Feb. 21, 1984

[51] Int. Cl.[4] .......... A61M 5/315

[52] U.S. Cl. .......... 604/210; 604/208; 222/309; 222/391

[58] Field of Search .......... 604/208, 209, 210, 211, 604/249; 222/309, 391

[56] References Cited

U.S. PATENT DOCUMENTS

| | | | |
|---|---|---|---|
| 3,337,095 | 8/1967 | Marbach et al. | 604/208 |
| 3,598,120 | 8/1971 | Mass | 604/208 |
| 3,905,365 | 9/1975 | Colombo | 222/309 |
| 4,022,207 | 5/1977 | Citrin | 604/209 |
| 4,072,254 | 2/1978 | Cox | 222/391 |
| 4,444,335 | 4/1984 | Wood et al. | 604/208 |

*Primary Examiner*—Melvyn J. Andrews

*Assistant Examiner*—Robert L. McDowell

*Attorney, Agent, or Firm*—Louis H. Reens

[57] ABSTRACT

A manually operated actuator is described with which small incremental motions of a rod are obtained to advance a piston of a prefilled syringe. The device employs a reciprocally actuated drive element with a hole through which the rod passes freely when the drive element is in a release position. When the drive element is pivoted to a rod engaging position a pair of edges formed by the hole engage the rod and advance it an increment depending upon the amount of linear movement of the drive element. A back-up inhibitor is employed to prevent the rod from moving back when the drive element is returned to a release position. The back-up inhibitor is syringe responsive by employing a mechanism which causes engagement of the rod by the inhibitor when a syringe is attached to the actuator housing. A syringe with specially adapted flanges is described for use with the actuator.

13 Claims, 22 Drawing Figures

INCREMENTAL ACTUATOR FOR SYRINGE

FIELD OF THE INVENTION

This invention generally relates to an incremental actuator. More specifically this invention relates to a manually operated actuator for incrementally moving a piston in a syringe.

BACKGROUND OF THE INVENTION

Syringe actuators are known in the art. See for example U.S. Pat. No. 4,022,207 to Paul S. Citrin wherein a syringe barrel is mountable to an actuator and the syringe piston is incrementally advanced. Although that actuator is accurate its piston advance is at fixed intervals.

SUMMARY OF THE INVENTION

With a manually operated actuator in accordance with the invention, incremental advances can be accurately controlled at any desired interval within a range and repeated with a high degree of accuracy. This is obtained as described with respect to one embodiment in accordance with the invention with a reciprocating mechanism formed with an elongate rod that is mounted to freely move past closely spaced guide surfaces associated with a housing. The rod is held in releasable positions by applying an edge of a pivoted back-up inhibitor to a rod surface with the holding force being sufficiently low so as to enable the rod to slide past the inhibitor edge. A drive element is positioned so that an edge of it can be brought from a release position into driving contact with a rod surface to slide the rod an increment whose magnitude depends upon the amount of motion of the drive element. The magnitude of the drive element motion is selectable.

With an acutator mechanism in accordance with the invention, a prefilled syringe containing a liquid to be dispensed below a piston can be safely applied to the housing, with the freely moving rod initally lightly seated onto the piston until a part of the syringe is so attached to the housing that it has caused the back-up inhibitor to engage the rod to hold it in position. The rod may then be incrementally moved to advance the piston and, thus, incrementally dispense liquid from the prefilled syringe.

The part of the syringe used to attach it to the housing may be a laterally extending flange that is shaped to conviently cause the retainer element to engage the rod as well as attach the syringe to the housing in a simple manner.

The incremental stroke of the rod can be set at any length within a range with an adjustable stop that is placed to regulate the motion of a pivotally movable operating lever. The lever in turn is coupled to the drive element so that it is first pivoted to place its edge against the rod and then moved to advance the rod by the desired increment.

With an actuator in accordance with the invention, the incremental motions of the rod are repeatable with a high degree of accuracy even with small motions. As a result, small equal sized liquid drops can be repeatedly dispensed.

It is, therefore, an object of the invention to provide a manually operatable actuator with which small incremental motions can be produced with high accuracy. It is a further object of the invention to provide a manually operated actuator for a prefilled syringe with which small drops of liquid can be dispensed with high repeatable accuracy.

These and other advantages and objects of the invention can be understood from the following description of a syringe actuator in accordance with the invention as described hereafter with reference to the drawings.

DETAILED DESCRIPTION OF THE DRAWINGS

Figure 1:
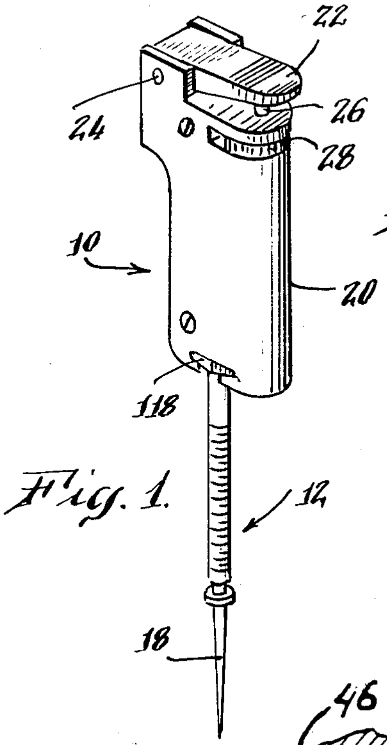
FIG. 1 is a perspective view of a manually operated actuator in accordance with the invention with a syringe mounted thereto.
Figure 12:
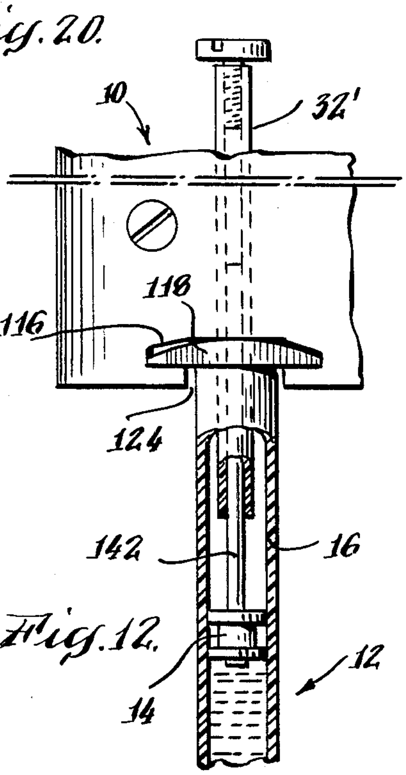
FIG. 12 is a partial side elevation broken away view of the part of the actuator of FIG. 1 and a syringe used therewith.

With reference to FIG. 1, a manually operated actuator 10, in accordance with the invention, is shown attached to a removable prefilled syringe 12 to control the movement of a piston 14, see FIG. 12, through a barrel portion 16 and thus, dispense drops of liquid. The syringe 12 may be of conventional shape with a needle 18 that may be an integral part of the syringe or with a needle that needs to be separately attached.

The syringe 12, may be prefilled with any suitable liquid desired to be dispensed. When it is a plastic, prefilled syringe 12 for a cyanoacrylate adhesive needle 18 preferable is made an integral part of syringe 12 and is opened by snipping off a tip portion.

Figure 2:
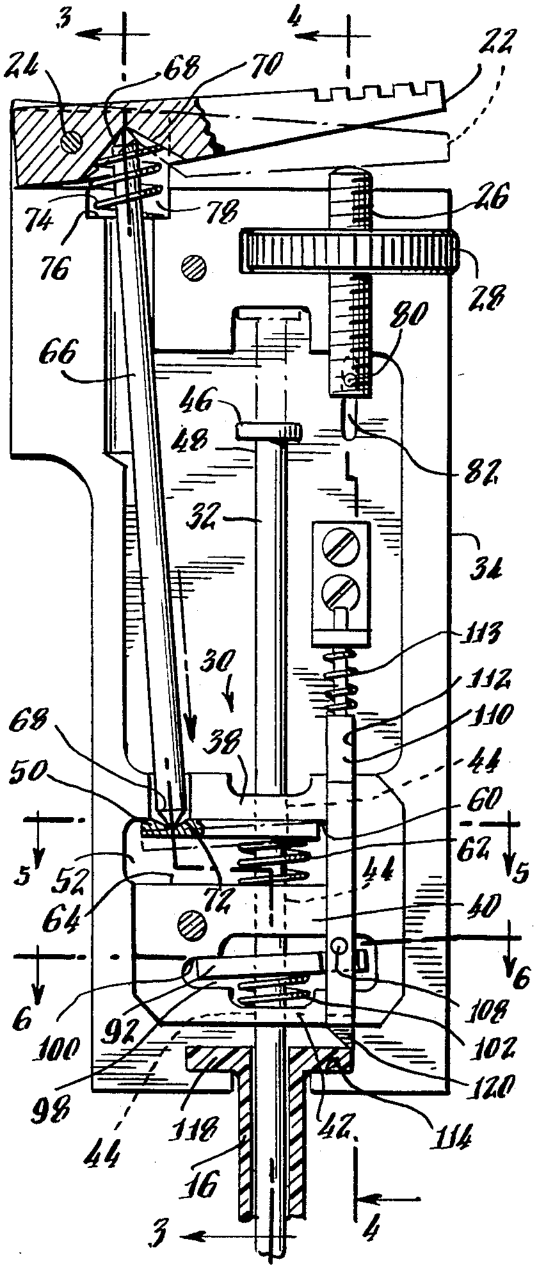
FIG. 2 is a side elevation section view of the actuator of FIG. 1.

Actuator 10 is shown in a form where a body portion of a housing 20 can be gripped by a single hand and operated by a thumb that is pivoted at 24 with the amount of pivot motion being regulatable with an adjustable stop 26, see FIG. 2, whose position is selected by a rotatable thumb control wheel 28, see FIG. 1.

Figure 14:
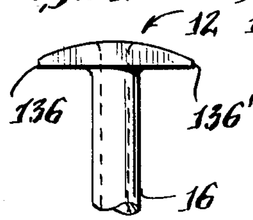
FIG. 14 is a partial side view of the top of the syringe barrel shown in FIG. 13.
Figure 3:
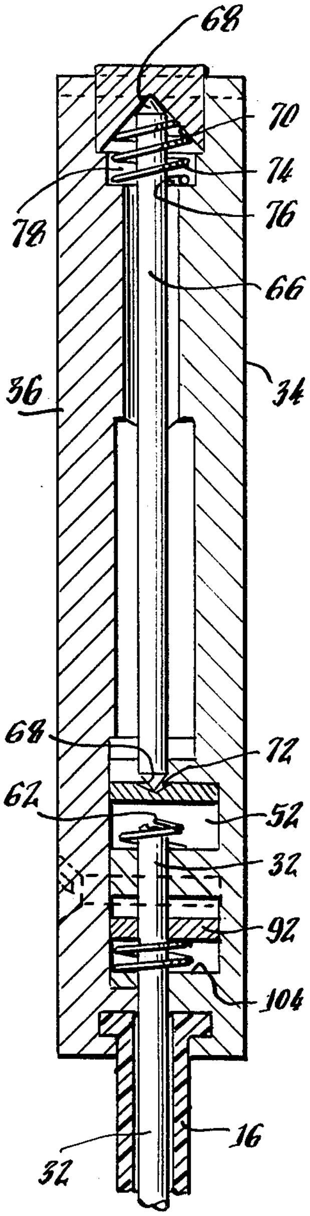
FIG. 3 is a section view of the actuator of FIG. 2 taken along the line 3—3 therein.
Figure 4:
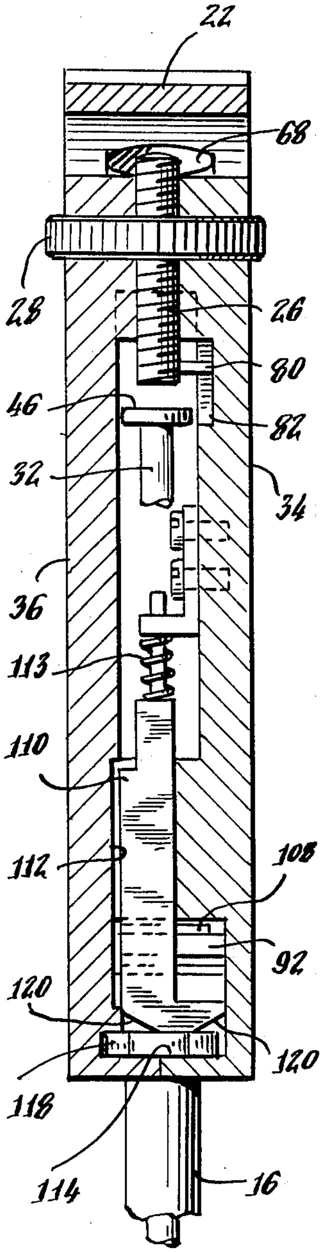
FIG. 4 is a section view of the actuator of FIG. 2 taken along the line 4—4 therein.

Actuator 10, as shown in FIGS. 2, 3 and 4, is formed with a housing 20 that encloses a reciprocating mechanism 30 with which an elongated metal rod 32 can be incrementally moved to, for example, move piston 14 in syringe barrel 16. Rod 32 may be solid or a hollow rigid tube as will be further explained with reference to FIGS. 13 and 14 and can be of any desired crossection. In the embodiment of FIGS. 2–4, rod 32 is solid and cylindrical in cross-section.

The housing 20 is formed of two mating sections 34, 36. Section 34 has mating projecting portions 38, 40 and 42, each of which has an aligned hole 44 through which rod 32 freely passes. Holes 44 are so sized that the walls of the holes 44 provide close fitting guide surfaces that permit free motion of the rod 32 along its longitudinal axis, yet limits its lateral motion. A screw 46 with an enlarged head is threaded into the end 48 of rod 32 to capture it inside housing 20.

The reciprocating mechanism 30 is formed with a plate shaped drive element 50 that fits with substantial tolerance inside a recess 52 between housing sections 38 and 40. The drive element 50 has one or several circular or curved drive edges 54, 54' (see FIGS. 7–10) formed by a cylindrical hole 56 through which rod 32 passes. Edges 54, 54' are formed by the intersection of the wall of the hole and the surfaces of the plate shaped drive element 50. Edges 54, 54' are thus located at opposite openings of hole 56. The diameter of hole 56 relative to the outer diameter of rod 32 is selected sufficiently large so that when drive element 50 is in a release position as illustrated in FIG. 2, rod 32 can freely pass through hole 56, yet hole 56 is made sufficiently small so that a small pivot movement of element 50 causes an engagement of drive edges 54, 54' with the peripheral surface of rod 32.

Generally, hole 56 is made larger than the diameter of rod 32 so that when drive element is inclined at an angle relative to rod 32, the edges 54, 54' can firmly grip the rod's peripheral surface. The angle at which this occurs can vary but preferably lies in the range from about 5 degrees to about 15 degrees, with the size of hole 56 being correspondingly selected.

Drive element 50 is seated against surface 60 of housing section 38 by a spring 62 seated on surface 64 of section 40. With the generally large tolerance fit of drive element 50 within recess 52, the element can be first pivoted so that both drive edges 54, 54' firmly engage rod 32 and then advanced away from surface 60 to move rod 32 a corresponding increment.

Operation of drive element 50 is obtained from the pivot actuation of lever 22 via a transfer rod 66 that has sharpened tips 68 at both ends, which respectively fit in an apex of a conically shaped recess 70 in lever 22 and one at 72 in drive element 50. Lever 22 is held in an upward position by a spring 74 seated between lever 22 around transfer rod 66 and the bottom wall 76 of a recess 78 in both housing sections 34 and 36.

The amount of pivot motion of lever 22 is regulated by stop 26, which is in the form of a screw that is threaded with thumb control wheel 28. Rotation of stop 26 is prevented by a pin 80 in stop 26 and which freely extends into a longitudinally extending guide slot 82 in housing section 34.

Since rod 32 can move freely along its longitudinal axis, with the drive element 50 in its release position as shown in FIG. 2, a device 90 is employed to hold rod 32. Device 90 could be a friction element. However, in such case, if rod 32 were in an extended position and a prefilled syringe were applied, the rod might prematurely exert an undesirably large amount of pressure against the piston 14 of the prefilled syringe 12 when this is affixed to the actuator 10.

Device 90, therefore, preferable is syringe responsive so that it does not hold rod 32 until after a syringe has been brought to its operating attachment position with actuator 10. Device 90 is formed with a plate-shaped back-up inhibitor 92 that operates in a similar manner with rod 32 as drive element, 50. Thus, back-up inhibitor 92 has retainer edges 94, 94' (see FIGS. 2, 7–10) formed by a hole 96 so that in a release position as illustrated in FIG. 7, the rod 32 can freely move along its longitudinal axis.

Back-up inhibitor 92 is located with substantial clearance in a recess 98 between housing segments 40, 42 and is spring biased towards a seating surface by a spring 102 seated between inhibitor 92 and the bottom wall 104. The seating surface is formed of a stationary surface 100 that is a part of housing 20 and a movable surface formed by a pin 108. In this manner, inhibitor 92 can be pivoted relative to stationary surface 100. Inhibitor 92 is normally biased towards a retainer position by spring 102 which urges inhibitor 92 against surface 100 as well as against a pin 108 penetrating and protruding from movable control lever 110. Control lever 110 is mounted to slidingly move along a slot 112 that is oriented generally parallel to the direction of motion of rod 32. Lever 110 is spring biased by a spring 113 towards a stop surface 114 in a mounting slot 116 in which a flange 118 of syringe 12 is placed to attach the syringe to actuator 10.

Control lever 110 has cam end surfaces 120 so that when syringe flange 118 is placed in slot 116 and is rotated against a cam surface 120, lever 110 is pushed away from stop surface 114. This in turn lifts pin 108 in the direction of arrow 121, see FIG. 8, away from spring 102 and allows spring 102 to pivot back-up inhibitor 92 relative to seating surface 100 in the direction of arrow 122, see FIG. 8. This pivot movement of inhibitor 92 causes its retainer edges 94, 94' to engage rod 32 and thus hold it while the drive element 50 alternately moves and releases rod 32.

Figure 7:
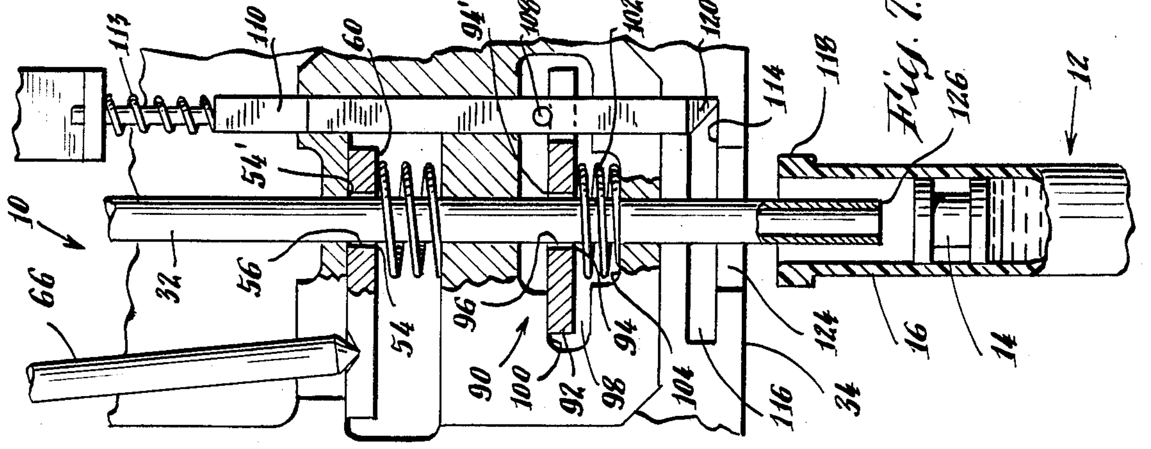

Operation of actuator 10 can be understood from FIGS. 7–10. In FIG. 7, the syringe 12 is not yet mounted to actuator 10 and, thus, rod 32 is free to move along its longitudinal axis because pin 108 has forced back-up inhibitor 92 into a release position when control lever 120 engages stop surface 114.

Figure 8:
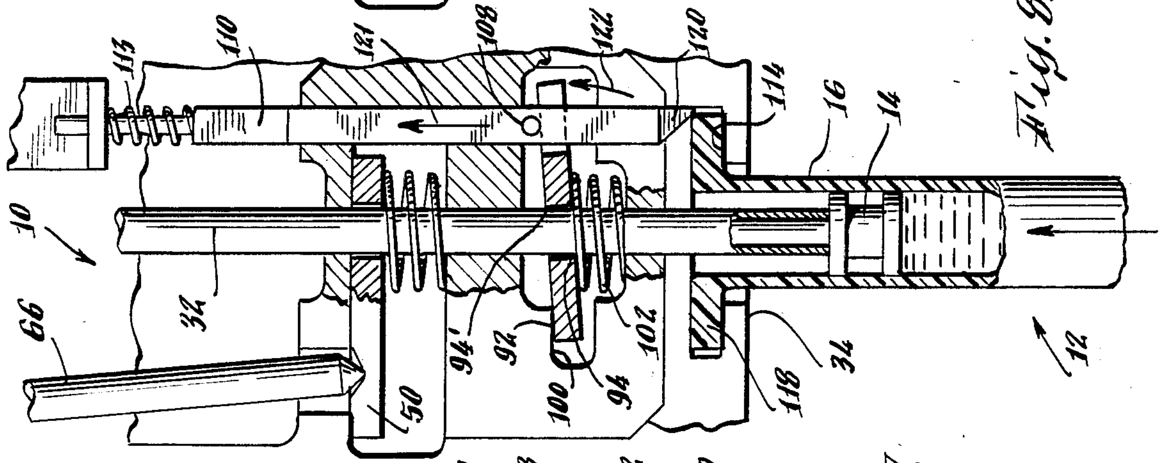

Syringe 12 is attached to actuator 10 by moving it through opening 124 into slot 116 while the freely movable rod 32 has its end 126 dropped into contact with piston 14 as shown in FIG. 8. When the flange 118 has entered slot 116, syringe 12 is rotated thus bringing flange 118 into contact with a cam surface 120 of lever 110 and, thus, force it away from surface 114. This causes inhibitor 92 to engage rod 32.

Figure 9:
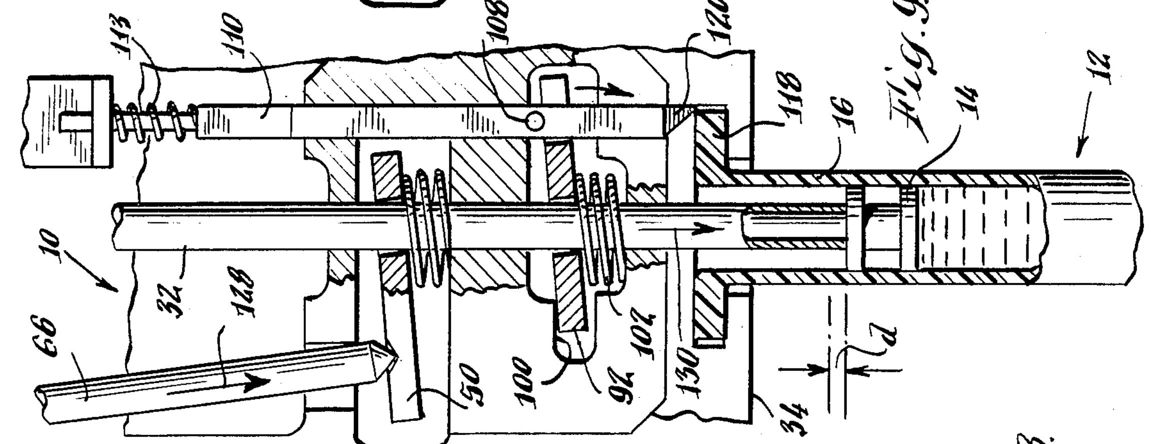

Rod 32 may now be incrementally advanced by actuating thumb control lever 22, see FIG. 2, and thus move transfer rod 66 in the direction of arrow 128, as shown in FIG. 9. This causes an initial pivot movement of drive element 50 and then an incremental advance of rod 32 in the direction of arrow 130.

Note that as rod 32 is advanced, its engagement with back-up inhibitor 92 tends to pivot it towards a release position. Rod 32 may thus advance in the direction of arrow 130 and slip past inhibitor 92 with little resistance from back-up inhibitor 92. Yet the latter remains very close to its pivoted rod engaging retaining position as suggested by the illustrated inclination of the inhibitor in FIG. 9.

Figure 10:
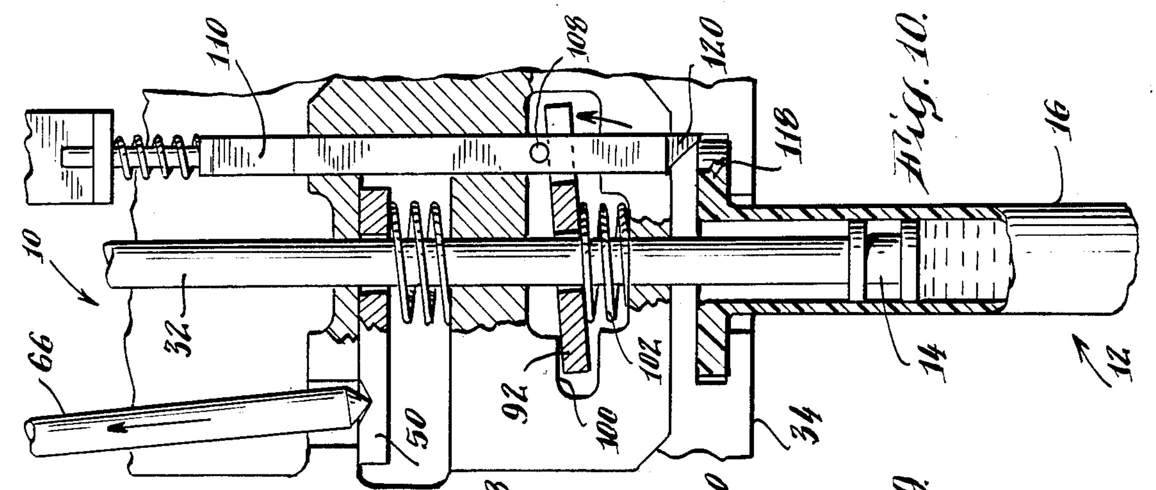
FIGS. 7, 8, 9 and 10 are partial side elevation section views of sequential operation of the actuator of FIG. 1.

When the actuating lever 22 and thus also transfer rod 66, are released to move in the direction of arrow 132 as shown in FIG. 10, any tendency by rod 32 to move back, such as from the spring action of a depressed piston 14, is immediately arrested by back-up inhibitor 92. Drive element 50, however, may return to its release position.

Hence, with an actuator 10 in accordance with the invention, the rod 32 and thus also piston 14 remain in a position where subsequent very small incremental movements of rod 32 deliver like sized drops of liquid from syringe 12. The actuator 10, thus enables precision delivery of drops with a high degree of repeatability.

With an actuator 10 in accordance with the invention, liquid drops can be delivered in an accurate manner from plastic polyethylene syringes capable of holding a cyanoacrylate adhesive. A relatively stiff piston 14, which is slightly oversized for the syringe barrel 16, may be used to provide a good hermetic seal in a barrel 16, yet can be accurately moved by actuator 10.

Figure 15:
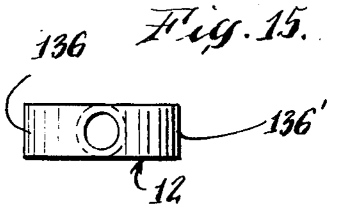
FIG. 15 is a top plan view of the syringe top of FIG. 14.
Figure 16:
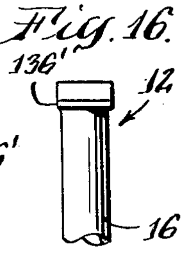
FIG. 16 is another side view of the syringe top of FIG. 14.
Figure 18:
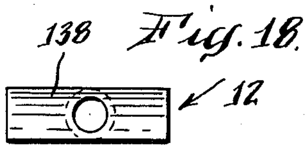
FIG. 18 is a top plan view of the syringe top of FIG. 17.
Figure 17:
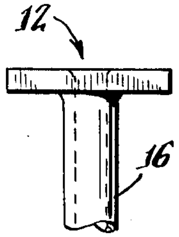
FIG. 17 is a partial side view of the top of a syringe barrel.
Figure 19:
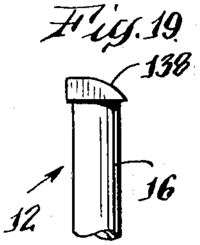
FIG. 19 is another side view of the syringe top of FIG. 17.
Figure 21:
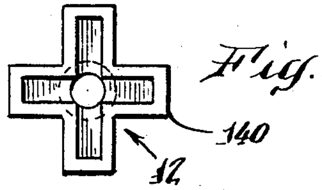
FIG. 21 is a top plan view of the syringe top of FIG. 20.
Figure 20:
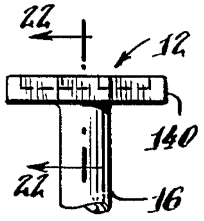
FIG. 20 is a partial side view in elevation of an alternate top of a syringe barrel.
Figure 22:
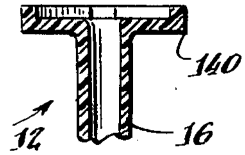
FIG. 22 is a section view of the syringe top of FIG. 20 taken along the line 22—22 therein.
Figure 11:
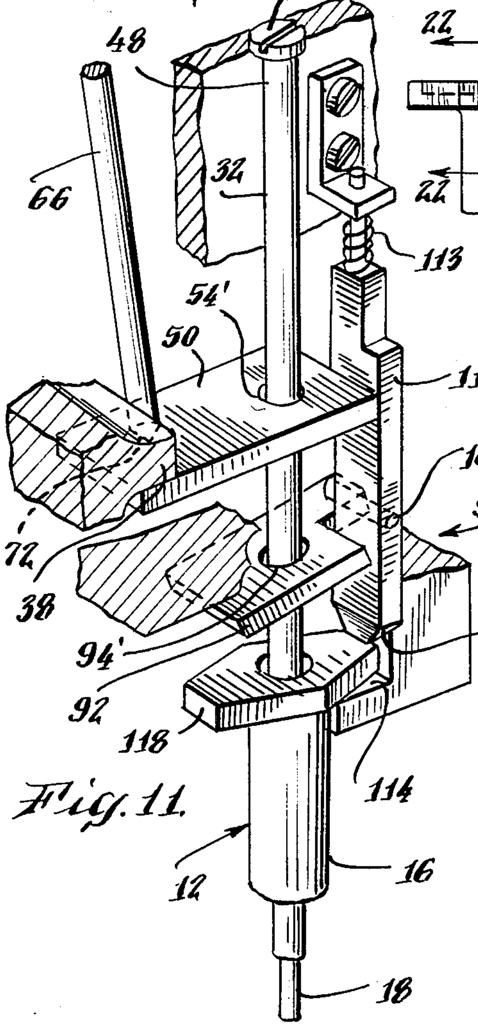
FIG. 11 is a perspective broken away view of the actuator of FIG. 1.
Figure 13:
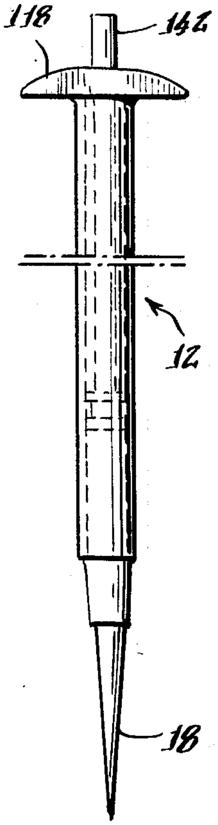
FIG. 13 is a side view in elevation of a syringe modified in accordance with the invention for use with the actuator of FIG. 1.
Figure 5:
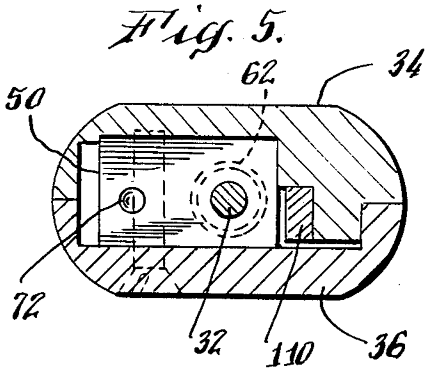
FIG. 5 is a section view of the actuator of FIG. 2 taken along the line 5—5 therein.
Figure 6:
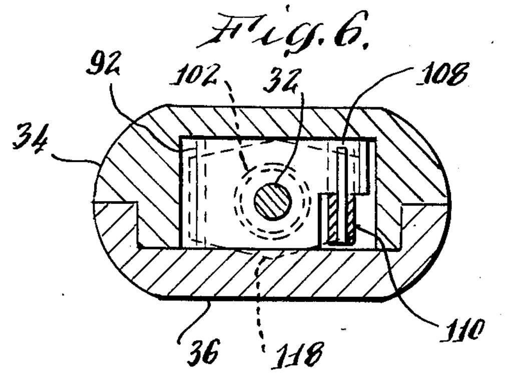
FIG. 6 is a section view of the actuator of FIG. 2 taken along the line 6—6 therein.

Having thus described a manually operated actuator in accordance with the invention, its advantages can be appreciated. Variation from the described embodiment can be implemented. For example, the operation of the drive element 50 and the back-up inhibitor 92 can be reversed so that repetitive operations of actuator 10 can cause a take-up of liquid with a syringe. The flange 118 of the syringe 12 may be modified to attach more easly to housing 20. For example, with reference to FIGS. 14–16, tapered flange ends 136, 136' are made thin enough to more easily wedge under the control lever 110. In such case, the thickness of ends 138 must still be sufficient to lift lever 110 and allow element 92 to hold rod 32. The flange ends may be shaped as shown in FIGS. 17–19, with a sloped cam edge 138. A cross-shaped flange 140, as shown in FIGS. 20–22 of desired thickness may be used. Syringe 12 may be provided with a piston 14, to which a shaft 142 is affixed as shown in FIGS. 12 and 13. Shaft 142 fits into a bore of a hollow rod 32'. The shape of housing 20 may be altered to provide a pistol-type grip with a rod 32 incremented in response to fore-finger movements on a trigger type lever.

What is claimed is:

1. A manually operated actuator for a prefilled syringe containing a piston which is to be incrementally moved comprising:

a housing;

an elongated rod mounted to the housing for movement along the longitudinal axis of the rod between a retracted and an extended position outside the housing and for effectively engaging the piston to move it within the syringe;

means for imparting incremental motion to the rod along its longitudinal axis;

said housing having a means for receiving and retaining a portion of said syringe with its piston in alignment with the rod so that movement of the rod will cause movement of the piston, back-up inhibitor means extending from said retaining means to said rod for operatively engaging the rod when a said syringe portion is held by the retaining means and disengaging from said rod in the absence of a said syringe portion from said retaining means so that said syringe piston can be brought into operative contact with the rod without movement of the piston until the syringe portion is held by the retaining means.

2. The actuator as claimed in claim 1, wherein said retaining means comprises a syringe mounting slot and wherein said back-up inhibitor means includes a back-up inhibitor and a movable control lever seated to enter the syringe mounting slot, said lever being effectively coupled to said back-up inhibitor to normally urge it towards a release position while enabling it to move to a retaining position in response to a syringe portion placed in said syringe mounting slot.

3. The actuator as claimed in claim 1 wherein siad retaining means includes: a syringe mounting slot in said housing, and located so that said rod passes through the slot; and further including: a syringe having a flange shaped to fit in said slot for attachment to the housing.

4. The actuator as claimed in claim 3, wherein said syringe flange has a cam surface to operate said means for causing movement of the back-up inhibitor.

5. The actuator as claimed in claim 1, wherein said rod is hollow and open at one end near the piston.

6. The actuator as claimed in claim 1 and further including a prefilled syringe for use with the actuator and having a barrel for containing a liquid to be dispensed and a piston in the barrel to dispense the liquid with, said barrel being open at one end to enable operative engagement of said rod with the piston said retaining means including a recess sized and shaped to receive and retain said syringe portion; said syringe having a flange attached to the barrel and being shaped to fit into said retaining means for retention thereby and wherein said flange acts as said syringe portion to actuate said back-up inhibitor means when placed in said recess of the retaining means.

7. The actuator and prefilled syringe as claimed in claim 6, wherein the retaining means includes a lever with a cam surface extending into the retaining means for contact with said syringe flange for activation of the back-up inhibitor means.

8. The actuator and prefilled syringe as claimed in claim 7, wherein the flange has a cam surface shaped to operatively engage said lever cam surface.

9. A manually operated actuator for a prefilled syringe containing a piston which is to be incrementally moved comprising:

a housing;

an elongated rod mounted to the housing for movement along the longitudinal axis of the rod between a retracted and an extended position and sized to engage the piston within the syringe;

a drive element movably mounted to the housing relative to a first seating surface, said drive element having a hole through which the rod passes, said hole having oppositely located drive edges past which the rod moves;

means for urging said drive element towards the first seating surface, with said hole being shaped so that the drive element at said first seating surface is in a release position enabling the rod to freely move through the hole of the drive element;

means for moving the drive element towards a pivoted position for engagement of said drive edges with the rod and for further linear incremental movement of the rod;

a back-up inhibitor movably mounted to the housing between release and rod retaining positions, means for forming a seating surface for said inhibitor, said latter seating surface comprising a stationary and a movable surface so that said inhibitor can be pivoted relative to the stationary surface;

means for urging said back-up inhibitor towards the seating surface;

said inhibitor having a hole through which the rod passes freely when said inhibitor is in its release position, said latter hole having a rod engaging edges and being sized to cause said edges to engage and retain the rod when the inhibitor is pivoted relative to the stationary seating surface; and means responsive to a syringe mounted to the housing for moving said movable surface to cause said inhibitor to retain the rod.

10. The actuator as claimed in claim 9, wherein said means for urging said back-up inhibitor is oriented to urge the inhibitor in a direction that is towards a retracted position of the rod.

11. The actuator as claimed in claim 10, wherein both said urging means comprise springs.

12. The actuator as claimed in claim 10, wherein said responsive means comprises a control lever movably mounted to the housing and having said movable surface, and means for urging said control lever towards a position where said movable surface places the inhibitor in its release position.

13. The actuator as claimed in claim 12, wherein said housing has a syringe mounting slot with a stop surface, said control lever being located to enter said slot and seat on the latter stop surface, said lever further having a cam surface to lift the lever from the stop surface in response to the wedging action of a syringe being mounted to said housing.

* * * * *